United States Patent [19]
Haitko et al.

[11] Patent Number: 5,973,183
[45] Date of Patent: Oct. 26, 1999

[54] PHOSPHINE LIGAND PROMOTED SYNTHESIS OF TETRAARYLOXYALKANE

[75] Inventors: Deborah Ann Haitko; Marsha Mottel Grade, both of Schenectady; Kathryn Lynn Longley, Saratoga Springs; Robert Edgar Colborn, Schenectady, all of N.Y.

[73] Assignee: General Electric Company, Schenectady, N.Y.

[21] Appl. No.: 09/134,408

[22] Filed: Aug. 14, 1998

[51] Int. Cl.[6] .............................. C07C 68/00; C07C 41/60
[52] U.S. Cl. .......................... 558/274; 558/275; 568/592
[58] Field of Search .................................. 558/274, 275; 568/592

[56] References Cited

U.S. PATENT DOCUMENTS 5,504,238  4/1996  Colburn .................................. 558/274
5,663,406  9/1997  KIng, Jr. et al. ........................ 558/243

*Primary Examiner*—Michael G. Ambrose
*Attorney, Agent, or Firm*—Noreen C. Johnson; Douglas E. Stoner

[57] ABSTRACT

Addition of phosphine ligands can produce high yields of tetraphenoxymethane, TPM, and diphenylcarbonate, DPC, in short reaction times and improved reaction rates by a copper-induced condensation of phenol and carbon disulfide, $CS_2$. Either aromatic or aliphatic substituted phosphine ligands can be employed. The copper(I) oxide utilization is significantly improved in reactions containing phosphine ligands, such that yields exceeding 100% tetraphenoxymethane are observed. Some of the sulfur-containing byproduct is transferred to the phosphine in the form of phosphine sulfide.

7 Claims, 4 Drawing Sheets

PHOSPHINE LIGAND PROMOTED SYNTHESIS OF TETRAARYLOXYALKANE

FIELD OF THE INVENTION

This invention is directed to methods for making aryl orthocarbonates and diaryl carbonates which are useful in the preparation of polycarbonate resins by melt transesterification technology.

Manufacture of polycarbonate resins by melt transesterification of diaryl carbonates provides some important environmental advantages over the standard commercial process which employs a two phase reaction of phenol and phosgene. In addition, the melt process produces a product characterized by very low levels of contaminants which make them particularly suitable for use in optical applications such as the manufacture of compact discs.

Manufacture of polycarbonates by melt esterification of diaryl carbonate is not used extensively on a commercial scale because, at the present time, there is no satisfactory synthesis for the diaryl carbonate. Prior art methods for the synthesis of the diaryl carbonate includes direct phosgenation of a phenol in an organic medium. Another process involves a multi-step low conversion rate process using a catalyst such as a titanium catalyst and a third process involves the direct carbonylation of a phenol requiring a catalyst such as palladium that is difficult to recycle.

The present invention provides an improved method for producing tetraaryloxyalkanes such as tetraphenoxymethane from phenol and carbon disulfide in the presence of cuprous oxide and an aliphatic, cycloaliphatic or aryl phosphine ligand.

SUMMARY

Addition of phosphine ligands to a reaction mixture comprising a hydroxy compound, cuprous oxide, and carbon disulfide can produce high yields of tetraphenoxymethane, TPM, and diphenylcarbonate, DPC, in short reaction times and at improved reaction rates by copper-induced condensation of the hydroxy compound, such as phenol, and the carbon disulfide, $CS_2$. Aromatic, cycloaliphatic, or aliphatic substituted phosphine ligands can be employed. The copper (I) oxide utilization is significantly improved in reactions containing phosphine ligands, such that yields exceeding 100% tetraphenoxymethane were observed.

The invention provides an enhanced method for making tetraaryloxyalkane and diaryl carbonates such as tetraphenoxymethane and diphenyl carbonate from cuprous oxide, phenol, and carbon disulfide. The presence of as little as about 0.1 to about 10 mole percent of the phosphine ligand significantly increases the reaction rate and yield of tetraphenoxyalkane and diaryl carbonate. Phosphine amounts of about 1 to about 10 are preferred. The reaction is shown below, where the term ligand indicates an aliphatic, cycloaliphatic, or aromatic phosphine.

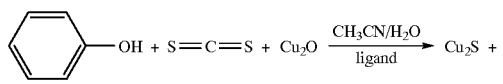

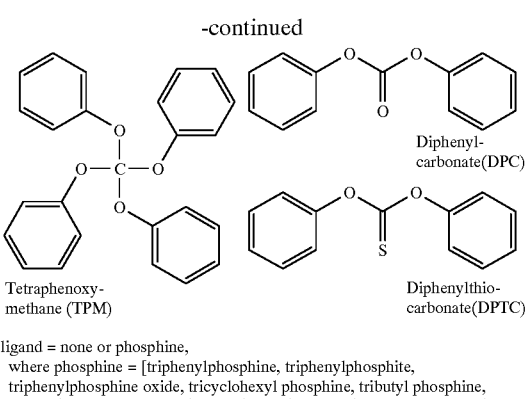

ligand = none or phosphine,
where phosphine = [triphenylphosphine, triphenylphosphite, triphenylphosphine oxide, tricyclohexyl phosphine, tributyl phosphine, 1,2-bis(diphenylphosphino)ethane(diphos), 1,2-bis(diphenylphosphino)butane]

DESCRIPTION OF THE INVENTION

This invention provides a method of producing carbonate ester comprising the step of mixing a hydroxy compound of the formula

R—OH, wherein R is selected from the group consisting of substituted and unsubstituted alkyl radicals, and substituted and unsubstituted aryl radicals; a sulfur compound selected from the group consisting of the formulas R'=C=S, and

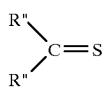

wherein R' is a divalent aliphatic radical, O or S, and R" is R or OR; and a promoter comprising at least one metal source that is capable of reacting with said hydroxy compound and said sulfur compound.

It has been discovered that the addition of small amounts of aromatic, aliphatic, or cycloaliphatic phosphines to the reaction admixture improves the yield of tetraphenoxymethane and diphenyl carbonate, DPC, from cuprous oxide, phenol, and carbon disulfide. Significant improvements in the rate of reaction were observed when phosphine ligands are present during the reaction. The reaction between cuprous oxide, phenol, carbon disulfide in the presence of low levels of methyl cyanide ($CH_3CN$), see reaction 116A, is compared with a similar reaction performed in the presence of about 10 mole percent triphenylphosphine, TPP, (reaction 131A) in Table 1. Once the reaction containing 10 mole percent triphenylphosphine (131A) undergoes an initial lag time of approximately 1.5 hours, the production of tetraphenoxymethane increases dramatically, with the total yield of tetraphenoxymethane, increasing from 5% to 105% within 5 hours.

Table 1 shows the data for control reactions that are cuprous oxide based with and without added water in addition to the data for the reactions that included various types and molar levels of phosphine-containing ligands. The table lists the auxiliary reagents used, the yield at 3 hours, the total yield at 30 hours, and the distribution of products.

When the reaction is carried out in the presence of water, diphenyl carbonate is generated insitu and becomes the primary product.

A similar reaction that used 1/10th the level of triphenylphosphine (1 mole percent triphenylphosphine; 35A) worked almost as well (Total Yield, Table 1) as the reaction containing 10 mole percent triphenylphosphine (131A). In fact, the reaction containing 1 mole percent triphenylphosphine (35A) exhibited a much reduced lag time. The lag time was reduced to 15 minutes for the reaction using 1 mole percent triphenylphosphine compared to a lag time of 1.5 hours for the 10 mole percent triphenylphosphine rxn. A graph comparing the first 7 hours of both reactions is shown in FIG. 2.

A reaction containing 10 mole percent triphenylphosphine with an added water phase (131B) showed an increase in the early rate of reaction, with a 75% yield by 3 hrs and a 95% yield by 4 hrs. The corresponding 1 mole percent triphenylphosphine reaction (35B) also demonstrated an enhanced rate of reaction of >80% by 3 hours. A graph comparing these reactions is shown in FIG. 3.

Aromatic bidentate phosphines as ligands have also been successfully employed to enhance the initial rate of tetraphenoxymethane and diphenyl carbonate production. These ligands have two aromatic phosphine groups linked by an aliphatic bridge. The two bidentate ligands screened were 1,2-bis(diphenylphosphino)ethane (also known as diphos) (reactions 919A & B, 1014A & B) and 1,4-bis (diphenylphosphino)butane (reactions 925A & B). The initial rate of reaction (see 3 hr. yield, Table 1) for these ligands is similar to that of triphenylphosphine.

Aliphatic phosphines as ligands have also been successful in increasing the rate and overall yield of tetraphenoxymethane and diphenyl carbonate from carbon disulfide, phenol and $Cu_2O$. Reactions utilizing tricyclohexyl phosphine, $(CyHex)_3$-P, as the added ligand at both 1 and 10 mole percent level (1024A & B; 927A & B) demonstrated a much improved reaction rate and yield. Surprisingly, even reaction 1029B, which used only 0.1 mole percent tricyclohexyl phosphine in combination with added water, gave a 3 hr yield of 90%. The first seven hours of the reactions, with added water, that contain all three levels of tricyclohexyl phosphine (0.1, 1, and 10 mole percent) are shown in FIG. 4.

In all of the reactions which contained high levels of phosphine ligands (10 mole percent) and achieved high total yields, significant levels of diphenylthiocarbonate (DPTC; half-product of the reaction) were observed in the early phase of the reaction. The levels of DPTC ranged from 25–50% based on copper from 3 to 7 hrs. In comparison, the fundamental $Cu_2O$-mediated reactions without ligands produce less than 1% of DPTC. Systems such as these (131A, 131B, 26B, 927B) demonstrate that some ligand-promoted reactions are capable of converting the half-product, DPTC, to tetraphenoxymethane insitu, thus efficiently completing the conversion from half-product to tetraphenoxymethane.

It has been noted, however, that lowering the level of ligand used in the reaction can have a positive effect on the rate. The phosphine ligand containing reactions which gave the best yield and fastest rate at the 10 mole percent level were also screened at the reduced level of 1 mole percent ligand. For all three of these ligands, (triphenyl phosphine: 35A & B, DiPhos: 1014A & B, tricyclohexyl phosphine: 1024A & B), less than 1% DPTC was noted throughout the reaction with little negative effect on the final yield of tetraphenoxymethane and diphenyl carbonate. Diphenylthiocarbonate, DPTC, which can be a precursor in the production of tetraphenoxymethane, is not always observed as a discrete intermediate on the path to tetraphenoxymethane. It is more efficient if the diphenylthiocarbonate half-product goes on to directly form tetraphenoxymethane so that an additional conversion step is not necessary. Therefore, reactions and conditions which produce little or no diphenylthiocarbonate by the end of the reaction are preferred.

Combined yields, consisting of tetraphenoxymethane, diphenyl carbonate and diphenyl thiocarbonate, of greater than 100% have been obtained in many of the cases where phosphine ligands are employed to increase the rate and reactivity of the copper-induced condensation of phenol with carbon disulfide. This enhancement of the overall reaction in the presence of phosphine ligands (greater than 100% yield based on copper) suggests that a catalytic pathway mediated by phosphines is a possible explanation.

Gas chromatography-mass spectrometer (GC-MS) analyses of the products of reactions which used high levels of phosphine ligands (10 mole percent) show that both the phosphine oxide and phosphine sulfide are produced during the reactions, concurrent with a decrease in the parent phosphine. The bidentate ligands themselves were too large to be observed by gas chromatography, therefore neither the oxide nor the sulfide were seen; it is assumed, however, that phosphine oxides and sulfides would also be produced in these cases.

A set of control reactions were done that utilized only triphenylphosphine (at a 50 mole percent level) in conjunction with phenol and carbon disulfide; i.e.—no cuprous oxide, $CU_2O$, was used. This set of reactions tested the catalytic ability of triphenylphosphine itself to convert carbon disulfide and phenol to tetraphenoxymethane while also evaluating if the conversion of triphenylphosphine to the phosphine oxide and phosphine sulfide occurred under typical reaction conditions. No reaction to tetraphenoxymethane occurred without cuprous oxide. Low levels of triphenylphosphine oxide, (TPP-O) and triphenylphosphine sulfide (TPP-S) were seen. However, when the amounts were compared to those in a cuprous oxide containing reaction, the level of TPP-O was one-fifth and the level of TPP-S was less than 1% without the use of cuprous oxide. This indicates that triphenylphosphine is capable of acting as a scavenger for sulfur, thus forming TPP-S during the conversion of carbon disulfide and phenol to DPTC and tetraphenoxymethane in the presence of cuprous oxide, so that not all of the sulfur is transferred directly to form cuprous sulfide, $Cu_2S$.

The metal oxide promoter for the condensation reaction is cuprous oxide ($Cu^{+1}$). The use of small amounts of aromatic or aliphatic phosphines as a ligand significantly improves the reaction rate and overall yield of tetraphenoxymethane and ultimately diphenyl carbonate.

The instant invention relates to a method for manufacturing carbonate ester, which is subsequently used to produce polycarbonate. More particularly, it relates to a method whereby carbonate ester is obtained by the metal induced reaction of a hydroxy compound with a sulfur compound. Products of the present invention include, but are not limited to, diphenyl carbonate, di(O-phenyl) thiocarbonate, and diethyl carbonate.

Hydroxy compounds useful in the present invention include materials represented by the formula:

R—OH, wherein R is selected from the group consisting of substituted and unsubstituted $C_{1-8}$ alkyl radicals, and substituted and substituted $C_{6-13}$ aryl radicals. It includes cresols, bisphenol-A, xylenols, p-cumyl phenol, n-alkylated phenols, halogenated phenols, and alcohols. Preferably, the hydroxy compound includes either substituted or unsubstituted phenol, or anhydrous ethanol.

For use in the instant invention, the sulfur compound comprises materials represented by formulas selected from the following:

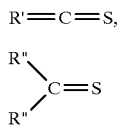

wherein R' is a divalent aliphatic radical, O, or S; and R" is R or OR; and wherein R is as previously defined. Suitable sulfur compounds include carbon disulfide and di (O-phenyl) thiocarbonate.

Addition of phosphine ligands can produce high yields of tetraphenoxymethane and diphenylcarbonate in short reaction times and with improved reaction rates by copper-induced condensation of phenol and carbon disulfide. Either aromatic or aliphatic substituted phosphine ligands can be employed. The copper(I) cuprous oxide utilization is significantly improved in reactions containing phosphine ligands, such that yields exceeding 100% tetraphenoxymethane are observed.

Water may be added to the reagents. Water may be added in a quantity sufficient to render it a co-solvent with the hydroxy compound, such as phenol, wherein a homogeneously mixed solution results. Water can also be added in an excess quantity sufficient to produce a two phase system with the hydroxy compound.

The materials can be reacted in either a batch or continuous process. They can be heated to a temperature of about 20–250° C. Preferably, they are heated to a temperature of about 45° to about 180° C.

The reactor can be operated at reflux or under pressure. The pressure can range from atmospheric pressure to about 20 Mpa. Preferably, the pressure is held in the range of atmospheric pressure to 1 Mpa. The reaction atmosphere can comprises air or an inert gas, such as argon or nitrogen. The reagents should be mixed sufficiently to make a heterogeneous slurry.

The total reaction time is dependent in part on temperature and on the desired degree of completion of the reaction. The required reaction time is determinable by one skilled in the art.

The materials produced by the present invention can be reacted under melt conditions with substantially no solvent present among the reagents. The process of the instant invention can also be run in the presence of a solvent. Suitable solvents are well known in the art. They include hydrocarbons such as toluene, xylenes, hexanes, heptanes, and octanes; acetonitrile; benzonitrile; ethers such as tetrahydrofuran, ether, dibutyl ether, and methyl butyl ether methyl ethyl ketone; acetone; methyl isobutyl ketone; chlorinated hydrocarbons such as chlorobenzenes and dichlorobenzenes; nitromethane; and nitrobenzene.

Alternatively, orthocarbonate can be generated by the method of the instant invention. The orthocarbonate comprises materials represented by the formula:

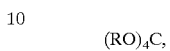

wherein each R is as previously defined.

When orthocarbonate is generated, the method of the instant invention comprises a further step of converting the orthocarbonate to a carbonate ester. When the method is used to generate orthocarbonate as a precursor to carbonate ester, it is preferable to remove water formed during the reaction of the promoter, hydroxy compound and sulfur compound. This elimated any potential hydrolysis during preparation of the orthocarbonate. This orthocarbonate can subsequently be used to produce a carbonate ester by acidic hydrolysis.

Ligands include compounds derived from phosphine by replacement of hydrogen atoms with alkyl or aryl substituents.

Illustrative phosphines include triphenyl phosphine, triphenyl phosphite, triphenyl phosphine oxide, tricyclohexyl phosphine, tributyl phosphine, 1,2-bis(diphenylphosphino) ethane, and 1,2-bis(diphenylphosphino)butane.

TABLE 1

Figure 1:
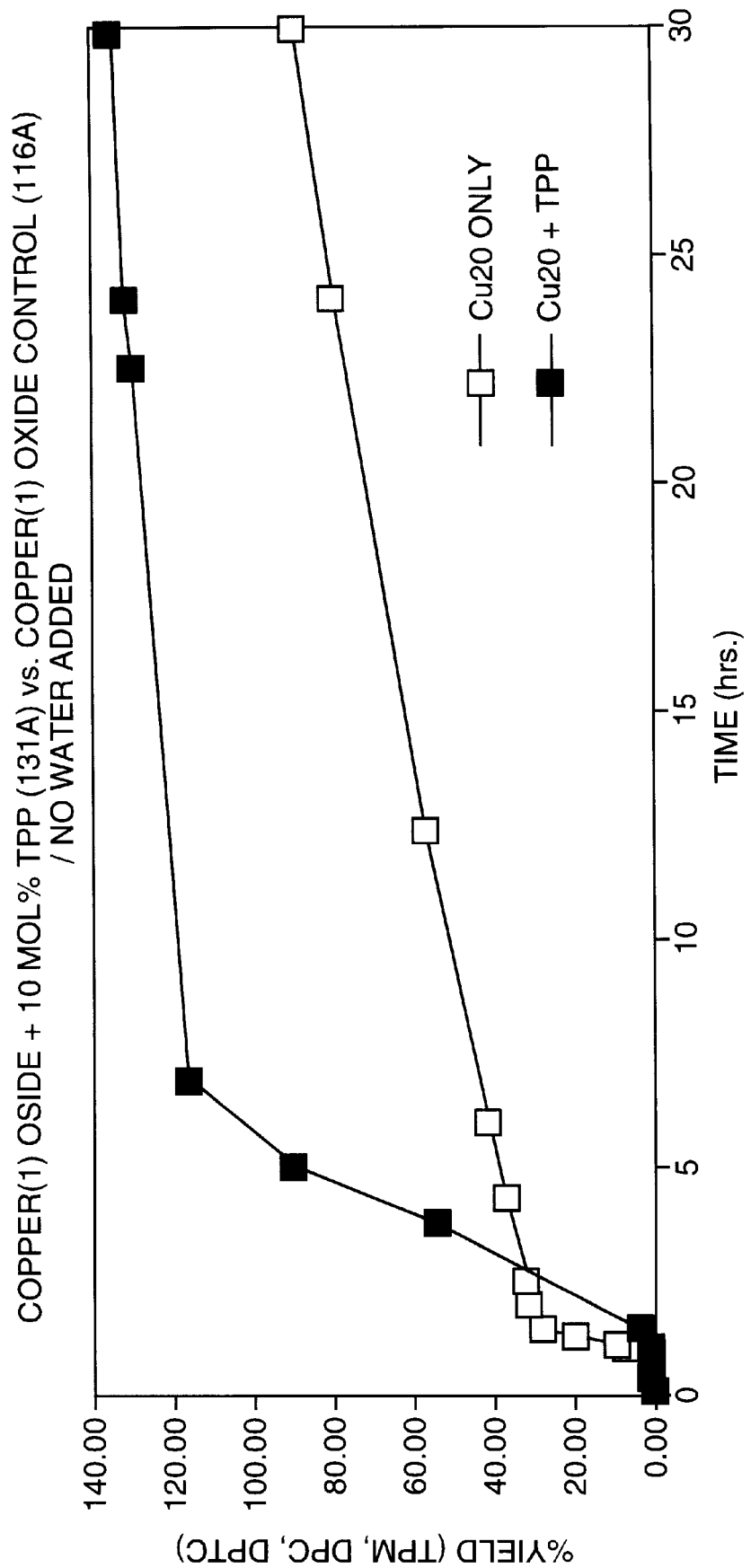
FIG. 1. Comparison Between Reactions using cuprous oxide, phenol and carbon disulfide to Form tetraphenoxymethane; With (131A) and Without (116A) 10 mol % Triphenylphosphine (TPP).
Figure 2:
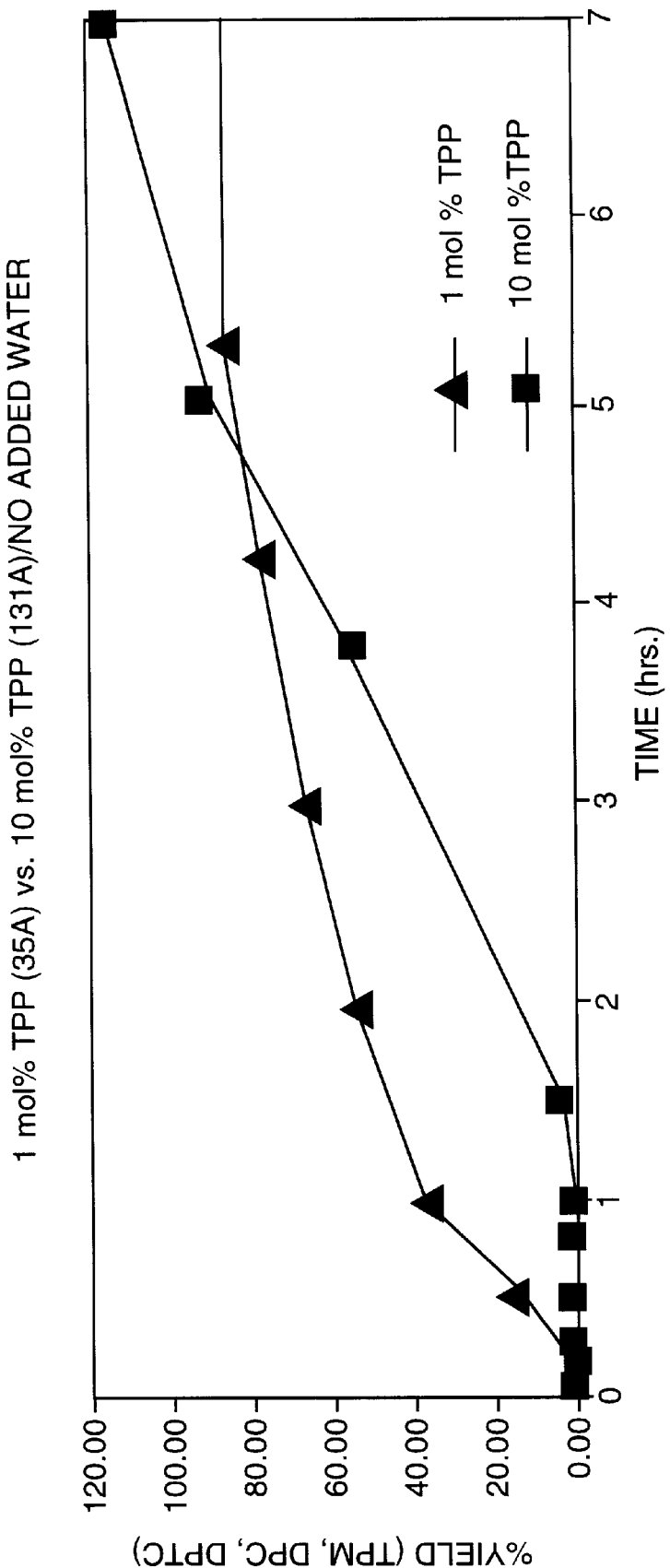
FIG. 2: Comparison Between Reactions using cuprous oxide, phenol and carbon disulfide along with the ligand Triphenylphosphine (TPP) to Form tetraphenoxymethane; no water added 1 mol % triphenylphosphine (35A) vs. 10 mol % triphenylphosphine (131A).
Figure 3:
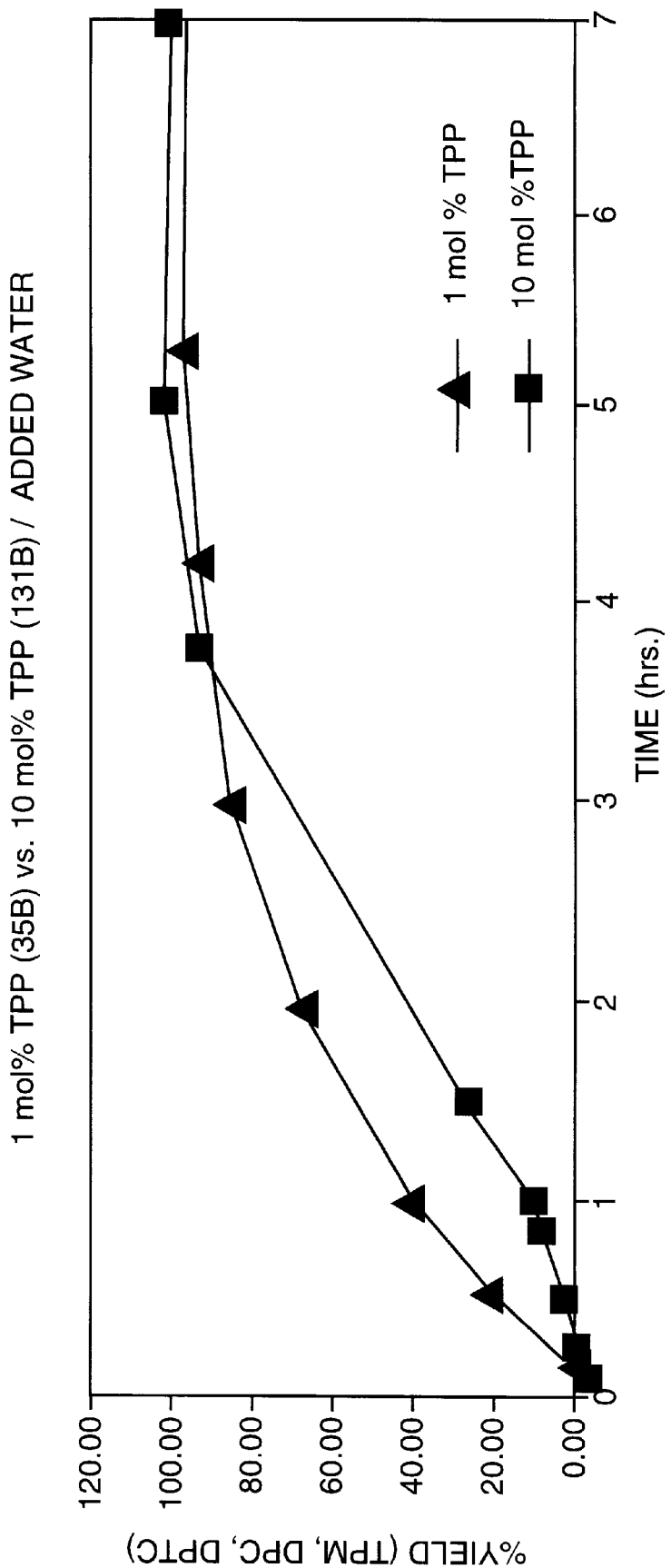
FIG. 3: Comparison Between Reactions using cuprous oxide, phenol and carbon disulfide along with the ligand Triphenylphosphine (TPP) to Form tetraphenoxymethane; water added 1 mol % triphenylphosphine (35B) vs. 10 mol % TPP (131B).
Figure 4:
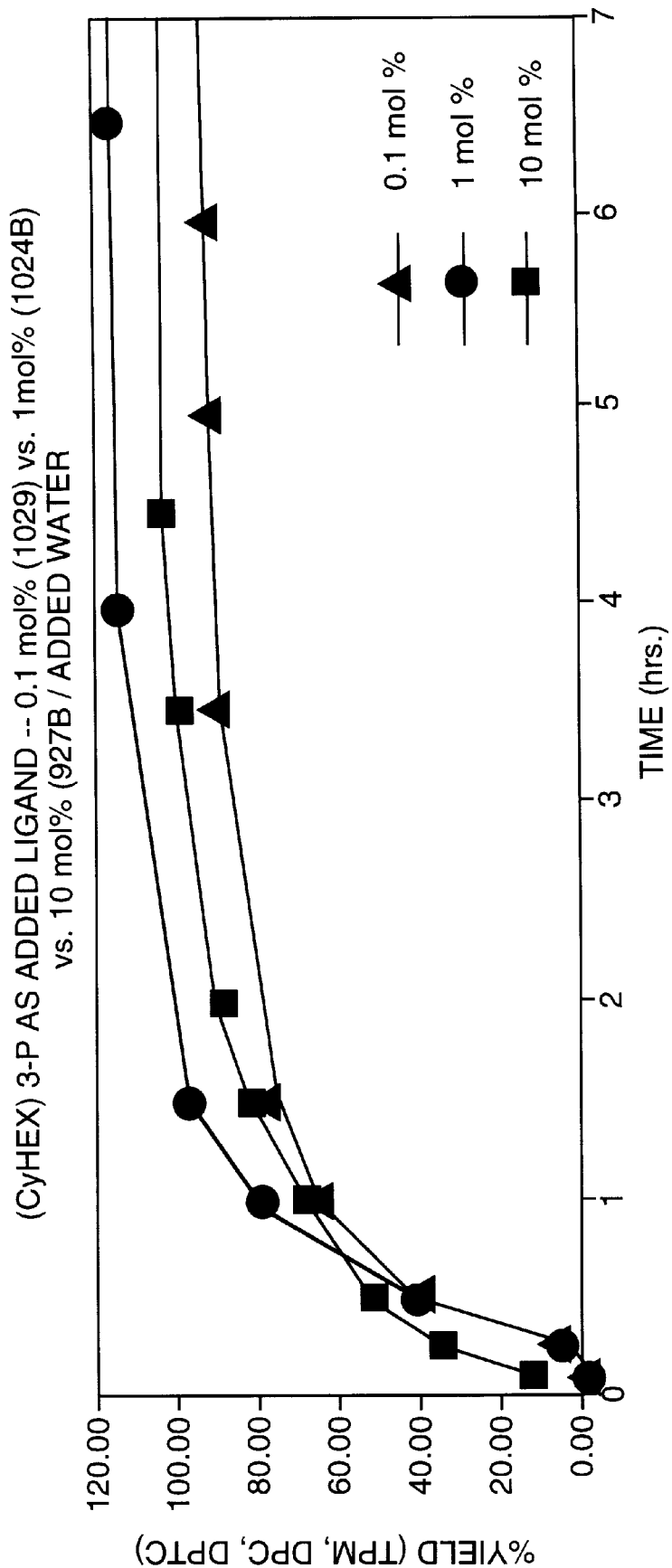
FIG. 4: Comparison Between Reactions using cuprous oxide, phenol and carbondisulfide along with the ligand Tricyclohexyl phosphine (tricyclohexyl phosphine) to form tetraphenoxymethane; water added ADDED; 0.1 mol % (CyHex)$_3$P (1029B), 1 mol % (CyHex)$_3$P (1024B), and 10 mol % (CyHex)$_3$P (927B).

Melt reactions of Cu$_2$O with phenol and CS$_2$; Control reactions and reactions containing aromatic and aliphatic phosphines as ligands

| Reaction* | ligand | ACN? | H$_2$O | 3 hr yield | Total Yield (30 h) | TPM/DPC** |
|---|---|---|---|---|---|---|
| 116A (Control) | — | Y | N | 34% | 95% | 93/2% |
| 116B (Control) | — | Y | Y | 34% | 78% | 21/57% |
| 131A | 10 mol % TPPhosphine | Y | N | 35% | 135% | 129/6% |
| 131B | 10 mol % TPPhosphine | Y | Y | 75% | 105% | 46/59% |
| 26A | 10 mol % TPPhosphine | N | N | 1.5% | 95% | 58/2% |

TABLE 1-continued

Melt reactions of $Cu_2O$ with phenol and $CS_2$; Control reactions and reactions containing aromatic and aliphatic phosphines as ligands

| Reaction* | ligand | ACN? | $H_2O$ | 3 hr yield | Total Yield (30 h) | TPM/DPC** |
|---|---|---|---|---|---|---|
| 26B | 10 mol % TPPhosphine | N | Y | 34% | 86% | 38/23% |
| 114A | 10 mol % TPPhosphine*** | Y | N | 57% | 125% | 70/5% |
| 35A | 1 mol % TPPhosphine | Y | N | 65% | 110% | 106/4% |
| 35B | 1 mol % TPPhosphine | Y | Y | 84% | 111% | 69/42% |
| 919A | 10 mol % diphos | Y | N | 70% | 113% | 63/0% |
| 919B | 10 mol % diphos | Y | Y | 62% | 93% | 57/16% |
| 1014A | 1 mol % diphos | Y | N | 72% | 86% (24h) | 84/2% |
| 1014B | 1 mol % diphos | Y | Y | 42% | 69% (24h) | 36/33% |
| 925A | 10 mol % ($Ø_2P$-$C_4$-$PØ_2$) | Y | N | 34% | 112% | 32/2% |
| 925B | 10 mol % ($Ø_2P$-$C_4$-$PØ_2$) | Y | Y | 34% | 59% | 20/12% |
| 927A | 10 mol % $(CyHex)_3$-P | Y | N | 75% | 106% (70h) | 53/3% |
| 927B | 10 mol % $(CyHex)_3$-P | Y | Y | 95% | 100% (70h) | 50/48% |
| 1024A | 1 mol % $(CyHex)_3$-P | Y | N | 117% | 120% | 117/3% |
| 1024B | 1 mol % $(CyHex)_3$-P | Y | Y | 105% | 114% | 57/57% |
| 1029A | 0.1 mol % $(CyHex)_3$-P | Y | N | 40% | 89% | 84/5% |
| 1029B | 0.1 mol % $(CyHex)_3$-P | Y | Y | 90% | 106% | 33%/73% |
| 1017A | 10 mol % Tributylphosphine | Y | N | 55% | 70% | 56/6% |
| 1017B | 10 mol % Tributylphosphine | Y | Y | 45% | 58% | 24/22% |
| 311A | 10 mol % TPPhosphite | Y | N | 22% | 42% | 19/19% |
| 311B | 10 mol % TPPhosphite | Y | Y | 36% | 51% | 12/39% |
| 102A | 10 mol % TPPhosphine Oxide | Y | N | 43% | 53% (23h) | 53/0% |
| 102B | 10 mol % TPPhosphine Oxide | Y | Y | 36% | 36% (23h) | 15/21% |

*All reactions were run at 65° C. under $N_2$, with mechanical stirring.
**Remainder of yield is DPTC.
***Addition of 3 g of mol. sieves (3Å) to remove any water formed during reaction.

EXPERIMENTAL

The melt reactions were run by combining phenol, cuprous oxide, phosphorus-containing ligand, internal standards, and a small amount of acetonitrile in a round bottom flask; some of the reactions contained water as a second phase. These reagents were stirred for 5 minutes at 45° C. under a nitrogen blanket in order to melt the phenol and disperse the cuprous oxide. The carbon disulfide was added and the temperature was concurrently raised to 65° C., where it was kept for the duration of the reaction. Representative reactions and their charges are included below. The reagents were used as received with no drying or pre-purification steps.

Cuprous Oxide ($Cu_2O$), Phenol, $CS_2$ and 10 mole % Triphenylphosphine (TPP) as added Ligand, ($CH_3CN$, no $H_2O$) (131A)

Into a 250 mL, 3-neck round bottom flask, equipped with an overhead stir paddle, condenser and nitrogen blanket, were placed phenol (30.02 g; 0.319 mol), cuprous oxide (1.5043; 0.01051 mol), triphenyl phosphine (0.555 g; 0.002116 mol, 10 mol % based on $Cu^+$), acetonitrile (2.5 mL; 0.04787 mol), and internal standards [3-methyl anisole (0.3123 g) and biphenyl (0.3104 g)]. The flask was lowered into a 45° C. oil bath and stirring was commenced. The reaction was mixed, while the phenol melted, for 5 minutes prior to the addition of the carbon disulfide, $CS_2$. The carbon disulfide was added (2 mL; 0.3325 mol) and the temperature of the oil bath was immediately raised to 65° C. for the duration of the reaction (120 h). The stir speed was fast to ensure good mixing of the heterogeneous mixture. During the course of the reaction, it changed from a dark red suspension to a well dispersed black suspension as the dark red $Cu_2O$ was converted to black $Cu_2S$. Samples were taken every 15–30 min. for the first three hours and intermittently thereafter. 0.4 mL samples were pipetted out, diluted with 1.5 mL $CH_3CN$, followed by filtration using Whatman Uniprep filters, containing a 0.45 μm PTFE membrane. Samples were analyzed using a Hewlett Packard 5890 Series II gas chromatograph equipped with a 30 meter DB-1 coated capillary column and a flame ionization detector (FID).

Cuprous Oxide ($Cu_2O$), Phenol, $CS_2$ and 10 mole % Triphenylphosphine (triphenylphosphine) as added Ligand, ($CH_3CN$, $H_2O$) (131B)

Into a 250 mL, 3-neck round bottom flask, equipped with an overhead stir paddle, condenser and nitrogen blanket, were placed phenol (30.04 g; 0.319 mol), cuprous oxide (1.5025; 0.01050 mol), triphenyl phosphine (0.5575 g; 0.002126 mol, 10 mol % based on $Cu^+$), acetonitrile (2.5 mL; 0.04787 mol), water (36 mL; 2.0 mol), and internal standards [3-methyl anisole (0.3018 g) and biphenyl (0.3018 g)]. The flask was lowered into a 45° C. oil bath and stirring was commenced. The reaction was mixed, while the phenol melted, for 5 minutes prior to the addition of the carbon disulfide, $CS_2$. The carbon disulfide was added (2 mL; 0.3325 mol) and the temperature of the oil bath was immediately raised to 65° C. for the duration of the reaction (47 h). The stir speed was fast to ensure good mixing of the heterogeneous mixture. During the course of the reaction, it changed from a dark red suspension to a well dispersed black suspension as the dark red $Cu_2O$ was converted to black $Cu_2S$. Samples were taken every 15–30 min. for the first three hours and intermittently thereafter. 0.7 mL samples were pipetted out, diluted, filtered and analyzed as stated above.

Cuprous Oxide ($Cu_2O$), Phenol, $CS_2$ and 1 mole % Triphenylphosphine (triphenylphosphine) as added Ligand, ($CH_3CN$, $H_2O$) (35B)

Into a 250 mL, 3-neck round bottom flask, equipped with an overhead stir paddle, condenser and nitrogen blanket, were placed phenol (30.03 g; 0.319 mol), cuprous oxide (1.5110; 0.01056 mol), triphenyl phosphine (0.0587 g; 0.0002238 mol, 1 mol % based on $Cu^+$), acetonitrile (2.5 mL; 0.04787 mol), water (36 mL; 2.0 mol), and internal standards [3-methyl anisole (0.3196 g) and biphenyl (0.3060 g)]. The flask was lowered into a 45° C. oil bath and stirring was commenced. The reaction was mixed, while the phenol melted, for 5 minutes prior to the addition of the carbon disulfide, $CS_2$. The carbon disulfide was added (2 mL; 0.3325 mol) and the temperature of the oil bath was immediately raised to 65° C. for the duration of the reaction (47 h). The stir speed was fast to ensure good mixing of the heterogeneous mixture. During the course of the reaction, it changed from a dark red suspension to a well dispersed black suspension as the dark red $Cu_2O$ was converted to black $Cu_2S$. Samples were taken every 15–30 min. for the first three hours and intermittently thereafter. 0.7 mL samples were pipetted out, diluted, filtered and analyzed as stated above.

Cuprous Oxide ($Cu_2O$), Phenol, $CS_2$ and 10 mole % 1,2-bis(diphenylphosphino)ethane (DiPhos) as added Ligand, ($CH_3CN$, no $H_2O$) (919A)

Into a 250 mL, 3-neck round bottom flask, equipped with an overhead stir paddle, condenser and nitrogen blanket, were placed phenol (29.95 g; 0.318 mol), cuprous oxide (1.5071; 0.01053 mol), 1,2-bis(diphenylphosphino)ethane (DiPhos, 0.8351 g; 0.002096 mol, 10 mol % based on $Cu^+$), acetonitrile (2.5 mL; 0.04787 mol), and internal standards [3-methyl anisole (0.3073 g) and biphenyl (0.3048 g)]. The flask was lowered into a 45° C. oil bath and stirring was commenced. The reaction was mixed, while the phenol melted, for 5 minutes prior to the addition of the carbon disulfide, $CS_2$. The $CS_2$ was added (2 mL; 0.3325 mol) and the temperature of the oil bath was immediately raised to 65° C. for the duration of the reaction (27 h). The stir speed was fast to ensure good mixing of the heterogeneous mixture. During the course of the reaction, it changed from a dark red suspension to a well dispersed black suspension as the dark red $Cu_2O$ was converted to black $Cu_2S$. Samples were taken every 15–30 min. for the first three hours and intermittently thereafter. 0.4 mL samples were pipetted out, diluted, filtered and analyzed as stated above.

Cuprous Oxide ($Cu_2O$), Phenol, $CS_2$ and 10 mole % Tricyclohexyl phosphine (($CyHex)_3$-P) as added Ligand, ($CH_3CN$, no $H_2O$) (927A)

Into a 250 mL, 3-neck round bottom flask, equipped with an overhead stir paddle, condenser and nitrogen blanket, were placed phenol (29.29 g; 0.311 mol), cuprous oxide (1.5056; 0.01052 mol), Tricyclohexyl phosphine (tricyclohexyl phosphine), 0.7562 g; 0.002122 mol, 10 mol % based on $Cu^+$), acetonitrile (2.5 mL; 0.04787 mol), and internal standards [3-methyl anisole (0.3132 g) and biphenyl (0.3001 g)]. The flask was lowered into a 45° C. oil bath and stirring was commenced. The reaction was mixed, while the phenol melted, for 5 minutes prior to the addition of the carbon disulfide, $CS_2$. The carbon disulfide was added (2 mL; 0.3325 mol) and the temperature of the oil bath was immediately raised to 65° C. for the duration of the reaction (70 h). The stir speed was fast to ensure good mixing of the heterogeneous mixture. During the course of the reaction, it changed from a dark red suspension to a well dispersed black suspension as the dark red $Cu_2O$ was converted to black $Cu_2S$. Samples were taken every 15–30 min. for the first three hours and intermittently thereafter. 0.4 mL samples were pipetted out, diluted, filtered and analyzed as stated above.

Cuprous Oxide ($Cu_2O$), Phenol, $CS_2$ and 1 mole % Tricyclohexyl phosphine (($CyHex)_3$-P) as added Ligand, ($CH_3CN$, no $H_2O$) (927A)

Into a 250 mL, 3-neck round bottom flask, equipped with an overhead stir paddle, condenser and nitrogen blanket, were placed phenol (30.36 g; 0.322 mol), cuprous oxide (1.5163; 0.01060 mol), Tricyclohexyl phosphine (tricyclohexyl phosphine), 0.0766 g; 0.0002149 mol, 1 mol % based on $Cu^+$), acetonitrile (2.5 mL; 0.04787 mol), and internal standards [3-methyl anisole (0.3132 g) and biphenyl (0.3130 g)]. The flask was lowered into a 45° C. oil bath and stirring was commenced. The reaction was mixed, while the phenol melted, for 5 minutes prior to the addition of the carbon disulfide, $CS_2$. The carbon disulfide was added (2 mL; 0.3325 mol) and the temperature of the oil bath was immediately raised to 65° C. for the duration of the reaction (30 h). The stir speed was fast to ensure good mixing of the heterogeneous mixture. During the course of the reaction, it changed from a dark red suspension to a well dispersed black suspension as the dark red $Cu_2O$ was converted to black $Cu_2S$. Samples were taken every 15–30 min. for the first three hours and intermittently thereafter. 0.4 mL samples were pipetted out, diluted, filtered and analyzed as stated above.

We claim:

1. A method for making a diaryl carbonate which comprises contacting a hydroxyaromatic compound with carbon disulfide in the presence of a carbonylation effective amount of cuprous oxide and a reaction promoting amount of a phosphine ligand.

2. A method for making tetraaryloxy alkane which comprises contacting at least one hydroxyaromatic compound with carbon disulfide, a carbonylation effective amount of cuprous oxide, and a phosphine ligand in an amount sufficient to enhance formation of the tetraaryloxyalkane.

3. The method of claim 1 in which the ligand is an aliphatic, cycloaliphatic, or aromatic phosphine.

4. The method according to claim 3 in which the ligand is present in an amount of from about 0.1 to about 10 mol percent based on the number of moles of cuprous oxide.

5. The method according to claim 1 in which the reaction mixture includes auxiliary reagents selected from the group consisting of water and methylcyanide.

6. The method according to claim 1 in which the hydroxyaromatic compound is selected from the group consisting of unsubstituted phenols, cresols, xylenols, n-alkylated phenols, halogenated phenols, bisphenol A, and p-cumyl phenol.

7. The method according to claim 1 wherein the phosphine ligand is triphenylphosphine, tricyclohexylphosphine, triphenylphosphite, 1,2-bis(diphenylphosphino)ethane, tributylphosphine, triphenylphosphine oxide, or 1,2-(diphenylphosphino)butane.

* * * * *